(12) United States Patent
Fautz

(10) Patent No.: US 9,229,083 B2
(45) Date of Patent: Jan. 5, 2016

(54) MAGNETIC RESONANCE METHOD AND SYSTEM TO GENERATE AN OPTIMIZED MR IMAGE OF AN EXAMINATION SUBJECT

(75) Inventor: Hans-Peter Fautz, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 666 days.

(21) Appl. No.: 13/247,428

(22) Filed: Sep. 28, 2011

(65) Prior Publication Data

US 2012/0074939 A1    Mar. 29, 2012

(30) Foreign Application Priority Data

Sep. 29, 2010   (DE) .......................... 10 2010 041 659

(51) Int. Cl.
| | |
|---|---|
| G01R 33/48 | (2006.01) |
| G01R 33/28 | (2006.01) |
| G01R 33/561 | (2006.01) |
| A61B 5/055 | (2006.01) |
| G01R 33/565 | (2006.01) |

(52) U.S. Cl.
CPC ............. *G01R 33/5612* (2013.01); *A61B 5/055* (2013.01); *G01R 33/5659* (2013.01)

(58) Field of Classification Search
CPC ........... G01R 33/5659; G01R 33/5612; G01R 33/4835; G01R 33/5607
USPC ......................... 324/300–322; 600/407–422
See application file for complete search history.

(56) References Cited

U.S. PATENT DOCUMENTS

| | | | |
|---|---|---|---|
| 7,218,113 B2 | 5/2007 | Feiweier et al. | |
| 7,242,193 B2 | 7/2007 | Feiweier | |
| 2003/0073897 A1* | 4/2003 | Fautz | 600/410 |
| 2005/0083054 A1 | 4/2005 | Feiweier et al. | |
| 2005/0171422 A1 | 8/2005 | Zhang | |
| 2007/0145975 A1* | 6/2007 | Feiweier et al. | 324/307 |
| 2009/0033326 A1* | 2/2009 | Szyperski et al. | A61B 5/055 324/307 |
| 2009/0137897 A1* | 5/2009 | Balchandani et al. | 600/410 |
| 2009/0230957 A1* | 9/2009 | Park | 324/307 |
| 2010/0060277 A1 | 3/2010 | Nezafat et al. | |
| 2010/0239142 A1* | 9/2010 | Dannels et al. | 382/131 |
| 2011/0210736 A1* | 9/2011 | Abe | G01R 33/4835 324/309 |
| 2011/0215803 A1* | 9/2011 | Bitz et al. | 324/307 |
| 2012/0187947 A1* | 7/2012 | Morrell | 324/309 |
| 2012/0223706 A1* | 9/2012 | Hetherington et al. | 324/307 |
| 2012/0229136 A1* | 9/2012 | Stemmer | 324/307 |
| 2012/0319686 A1* | 12/2012 | Jesmanowicz et al. | A61B 5/055 324/309 |

OTHER PUBLICATIONS

"Fat-Suppressed Steady-State Free Precession Imaging Using Phase Detection," Hargreaves et al., Magnetic Resonance in Medicine, vol. 50 (2003) pp. 210-213.

* cited by examiner

*Primary Examiner* — Melissa Koval
*Assistant Examiner* — Rishi Patel
(74) *Attorney, Agent, or Firm* — Schiff Hardin LLP

(57) ABSTRACT

A magnetic resonance method and system for generation of an optimized MR image of an examination subject operate as follows. A pulse sequence including a series of at least two RF pulses is radiated into the examination subject to generate at least one optimized signal, wherein the second and possibly every additional RF pulse is radiated before the effect of the first or a preceding RF pulse on the spin system in the examination subject has decayed. The radiated RF pulses are generated by parallel transmission coils. At least the signal resulting after the last radiated RF pulse of the pulse sequence is acquired. The pulse sequence is repeated with modified spatial coding until signals have been generated and acquired in a desired positional space. The optimized MR image per pulse sequence is calculated from at least one of the acquired signals.

8 Claims, 3 Drawing Sheets

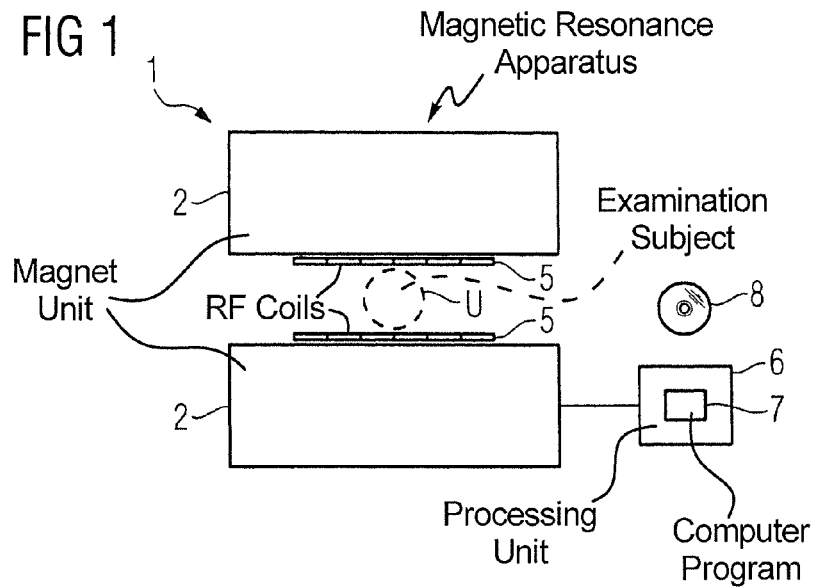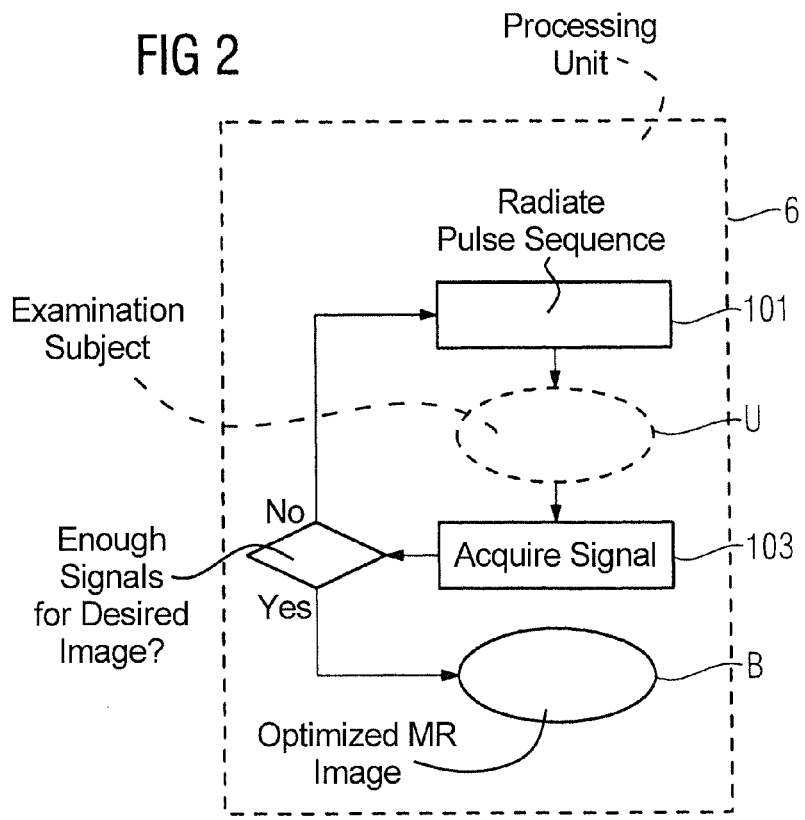

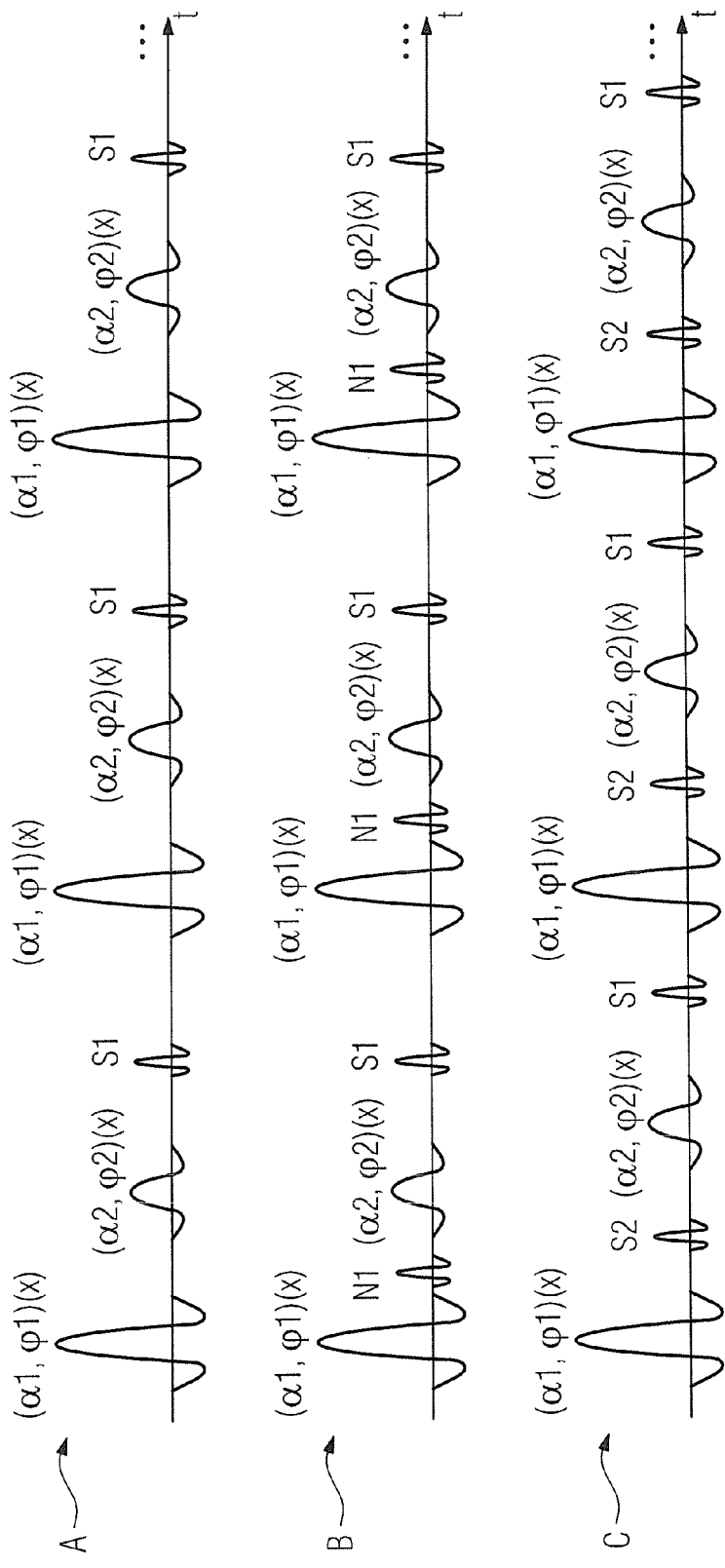

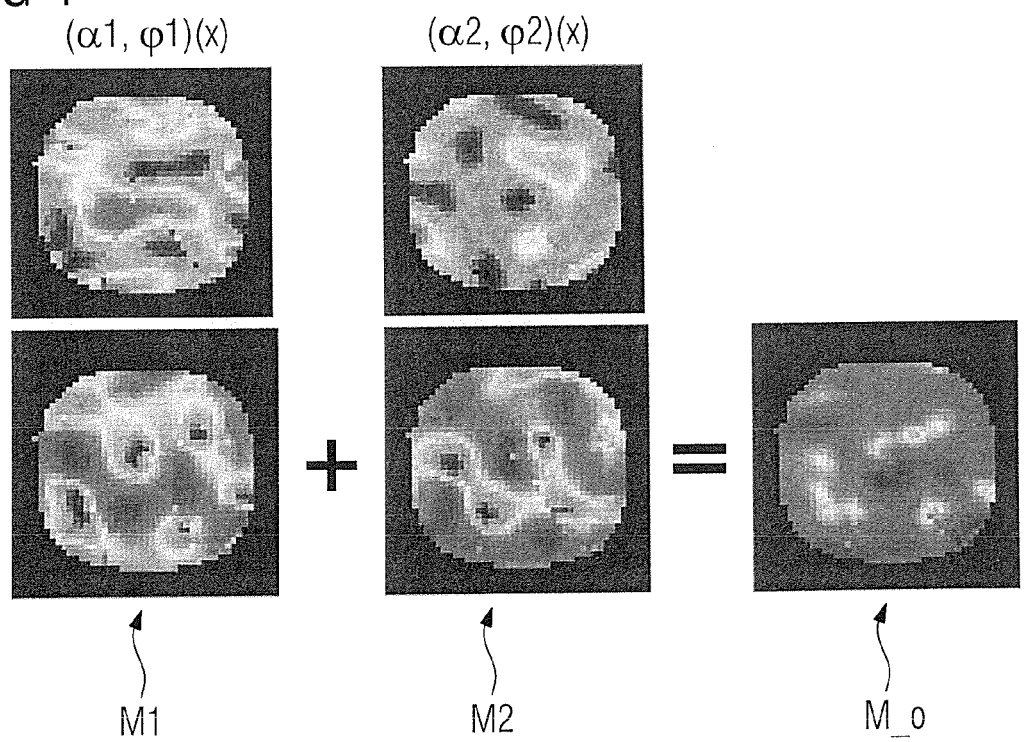

MAGNETIC RESONANCE METHOD AND SYSTEM TO GENERATE AN OPTIMIZED MR IMAGE OF AN EXAMINATION SUBJECT

BACKGROUND OF THE INVENTION

1. Field of the Invention

The present invention concerns a method to generate an optimized MR image of an examination subject, a corresponding electronically readable data storage medium, and a corresponding magnetic resonance apparatus.

2. Description of the Prior Art

Magnetic resonance (MR) imaging is a known modality with which images of the inside of an examination subject can be generated. Expressed in simple terms, for this purpose the examination subject is positioned in a strong, static, homogeneous basic magnetic field B0 (field strengths from 0.2 to 7 Tesla or more) in a magnetic resonance apparatus so that nuclear spins in the subject orient along the basic magnetic field. For spatial coding of the measurement data, rapidly switched gradient fields are superimposed on the basic magnetic field. To trigger nuclear magnetic resonances, radio-frequency excitation pulses (RF pulses) are radiated into the examination subject by at least one transmission coil. The triggered nuclear magnetic resonances (signals) are measured by reception coils, and MR images, for example, are reconstructed on the basis of the measured signals. The magnetic flux density of these RF pulses is typically designated with B1. The pulse-shaped radio-frequency field is therefore generally also called a B1 field for short. The nuclear spins of the atoms in the examination subject are excited by these radio-frequency pulses such that they are deflected (flipped) out of their steady state parallel to be basic magnetic field B0 by an amount known as an "excitation flip angle" (also called a "flip angle" in the following for short). The nuclear spins then precess around the direction of the basic magnetic field B0. The magnetic resonance signals that are thereby generated are acquired by radio-frequency reception antennas. The acquired measurement data are digitized and stored as complex numerical values—raw data—in a k-space matrix. By means of a multidimensional Fourier transformation, an associated MR image can be reconstructed from the k-space matrix populated by such values. In addition to anatomical images, spectroscopic data, movement (flow) data or temperature data of an examined or treated area can be determined using suitable magnetic resonance techniques.

The measured signals thus depend on the radiated RF pulses. In addition to a homogeneous basic magnetic field and precisely linear gradient magnetic fields for spatial coding, typical methods to reconstruct image data sets from magnetic resonance signals also require a homogeneous RF field distribution (B1 field distribution) in the examination volume. However, the B1 field distribution in the examination volume typically is non-uniform in real MR systems, which leads to image inhomogeneities (image artifacts in the MR images reconstructed from the signals, and therefore to a poorer ability to recognize the desired details in the imaged examination subject. Particularly in whole-body imaging or acquisitions of the torso (breast, abdomen, pelvis) at basic magnetic fields of 3 Tesla or more, artificial shadows occur in the image due to an inhomogeneous RF field distribution. Due to the resulting poor image quality, this has prevented more extensive use of such examinations in the clinical field. The interfering image artifacts intensify and multiply with an increase of the field strengths that are used.

Artifacts and inconsistencies in MR imaging or spectroscopy due to inhomogeneous B1 fields have long been known.

In conventional MR imaging with a transmission channel, it is not possible to directly affect the homogeneity of B1 fields. Therefore, conventional methods have the goal of exciting signals over a defined range of B1 variations, which signals are independent of the B1 field strength. One example of such a procedure is the use of composite RF pulses or adiabatic RF pulses. However, these have only limited applicability with regard to achievable flip angle and phase response in use with slice selection, as well as with regard to pulse times and SAR intensity (SAR: "specific absorption rate"). They are therefore typically used only for magnetization preparation and moreover have found no broad application in typical MR imaging sequences. Such magnetization preparations can in turn reduce the sensitivity of a subsequent imaging sequence, but they naturally lengthen the required transmission time of the complete pulse sequence.

A further known procedure attempts to achieve a spatial modulation of the generated transversal magnetization by simultaneous action of RF and gradient pulses on the spin system. The achievable homogeneity of these spatially selective, two-dimensional (2D) or three-dimensional (3D) pulses is unlimited in principle. 2D and 3D modulations, however, lead to very long pulse times and an inefficient use of the RF pulses since the average flip angle per radiated power is reduced. Most notably, the length of the required pulse sequences has previously prevented an establishment of this method in MR imaging.

Using the parallel transmission technique—thus using multiple transmission/reception coils—it is possible directly influence the spatial distribution of the B1 field. The individual RF fields thereby emanating in parallel from spatially separated individual transmission coils are vectorially superimposed in order to form the actual B1 field. The generated B1 field can be spatially modulated by adjusting the phases and amplitudes of the individual transmission channels (transmission coils). This method is known as "RF shimming". The achievable homogeneity is limited by the hardware, i.e. the number of available parallel transmission channels, for example. The pulse times for the spatially selective 2D and 3D pulses that are described above can also be shortened with the parallel transmission technique. However, the achievable pulse times are still longer than could be used to replace the previously typical slice-selective or non-selective pulses in the prevalent imaging sequences. Furthermore, it is unclear how robustly (i.e. with regard to B0 field variations, chemical shifts, movements of the examination subject and/or relaxation times), and with what SAR efficiency, these complex pulses can be used for in vivo imaging.

DE 103 38 074 B4 (corresponding to United States Patent Application Publication No. 2005/0083054) describes a method to compensate for contrast inhomogeneities in magnetic resonance images that are caused by spatial distributions of a transmitted radio-frequency field, in which method multiple individual images of a defined region are initially acquired with different radio-frequency pulse sequences which lead to different flip angles, and then on the basis of the various individual images a common contrast-homogenized image for the appertaining region is generated so that, within the contrast-homogenized image, intensity fluctuations caused by a distribution of the flip angle are at least smaller per region than in the individual images.

SUMMARY OF THE INVENTION

An object of the present invention is to provide a method, a non-transitory electronically readable data medium, and an imaging system with which an optimized MR image can be generated in a simple and quick manner.

The method according to the invention for generation of an optimized MR image of an examination subject proceeds as follows.

A pulse sequence that includes a series of at least two RF pulses is radiated into the examination subject to generate at least one optimized signal, wherein the second and possibly every additional RF pulse is radiated before the effect of the first or a preceding RF pulse on the spin system in the examination subject has decayed or subsided.

At least the signal resulting after the last radiated RF pulse of the pulse sequence is acquired.

The pulse sequence is repeated with modified spatial coding until signals have been generated and acquired in a desired positional space.

The optimized MR image per pulse sequence is calculated from at least one of the acquired signals.

By the radiation of the second (and possibly every additional) RF pulse into the examination subject before the effect of the first RF pulse on the spin system in the examination subject has decayed, the number of degrees of freedom available for the modeling of the B1 fields to be achieved is multiplied with the number of radiated RF pulses. Twice as many degrees of freedom are available for the optimization of two RF pulses than given only one RF pulse. The result of the magnetization excited by the second RF pulse on the spin system in the examination subject depends on the magnetization excited after the first RF pulse. Therefore there is the possibility to optimize the two RF pulses simultaneously, and there are more possibilities in the pulse design due to the increased number of degrees of freedom. If more than two RF pulses are radiated, this applies analogously. If a signal is acquired after each RF pulse and an individual image is respectively calculated from the signals per RF pulse, the individual images are dependent on one another. By the radiation of the RF pulses into the examination subject by means of parallel transmission coils—thus via multiple transmission channels—additional freedoms with regard to the selection of the RF pulses per pulse sequence can be used in order to generate additionally optimized signals more simply.

Prevalent RF transmission coils are fashioned for this purpose by means of a transmission/reception diplexer and can also be operated as reception coils, in which case parallel transmission coils can also be designated as parallel reception coils and be used to receive resulting signals.

The advantages and embodiments described for the method analogously apply to the electronically readable data medium and the magnetic resonance apparatus.

BRIEF DESCRIPTION OF THE DRAWINGS

FIG. 1 schematically illustrates a magnetic resonance apparatus designed to implement the method according to the invention.

FIG. 2 is a flowchart of an embodiment of a workflow of the method according to the invention.

FIG. 3 shows exemplary pulse sequences for implementation of the method.

FIG. 4 shows an example of a calculation of two images acquired from a first and second RF pulse to form an optimized MR image in accordance with the invention.

DESCRIPTION OF THE PREFERRED EMBODIMENTS

In FIG. 1 a magnetic resonance apparatus 1 is schematically represented by a magnet unit 2 and parallel RF transmission and/or reception coils 5. The basic design of a magnetic resonance apparatus composed of a magnet unit, radio-frequency coils and gradient coil unit as well as the associated control units of such a magnetic resonance apparatus are known and therefore need not be explained in detail herein.

During an MR examination (data acquisition) an examination subject—for example a region of a patient that is to be examined—is located in an examination volume U of the magnetic resonance apparatus 1. As described above, RF pulses are radiated into the examination subject located in the examination volume U in the course of the MR examination. The signals resulting in the examination subject due to the radiation of the RF pulses are acquired.

The magnetic resonance apparatus 1 is connected with a processing unit 6 which can receive data from the magnetic resonance apparatus 1 (in particular the signals acquired by the RF reception coils of the magnetic resonance apparatus 1) and can send data (for example control commands) to the magnetic resonance apparatus, in particular to the RF transmission coils.

When a computer program 7 encoded on a data storage medium 8 according to the invention is loaded into the programmable processing unit 6 of the magnetic resonance apparatus 1, the method described in the following can be executed when the instructions of commands embodied in the computer program 7 are executed in the processing unit 6.

The method according to the invention is explained in the following using FIGS. 2 and 3, with indication of exemplary, schematic pulse sequences (FIG. 3).

FIG. 2 schematically shows the workflow of the method. In a processing unit 6, at least one first and one second RF pulse are designed and selected per pulse sequence such that at least one optimized signal in an examination subject can be generated with these RF pulses. In Step 101 the pulse sequence is radiated into an examination subject in an examination volume U, wherein the pulse sequence comprises the developed, selected series of at least two RF pulses. The second (and possibly every additional) RF pulse is radiated before the effect of the first or a preceding RF pulse on the spin system in the examination subject has faded away.

In a further Step 103, at least the signal resulting after the last radiated RF pulse of the pulse sequence is acquired and stored in the processing unit (for example) for later processing. For example, the pulse sequence is repeated with modified spatial coding until signals could be generated and acquired in a desired positional space. If a sufficient number of signals has been acquired in order to be able to acquire a desired image, an optimized MR image B is calculated from at least one of the acquired signals per pulse sequence. A few examples of from which signals optimized MR images can be calculated are indicated further below with reference to FIG. 3.

For example, the optimization of the RF pulses to generate at least one optimized signal can take place such that an image with a predetermined image contrast can be calculated from the acquired signals. For example, for this the RF pulses can generate signals that generate an optimally homogeneous magnetization in the examination subject.

Exemplary schemes A), B) and C) of possible RF pulses series of pulse sequences with, respectively, a first RF pulse $(\alpha 1, \phi 1)(x)$ (a with amplitude $\alpha 1$ and phase $\phi 1$ and a second RF pulse $(\alpha 2, \phi 2)(x)$ with amplitude $\alpha 2$ and phase $\phi 2$ and associated resulting signals (echoes) S1, S2 and N1 are presented in FIG. 3, wherein (x) stands for the spatial dependency of the flip angle distribution $(\alpha 1, \phi 1)(x)$ or $(\alpha 2, \phi 2)(x)$; in other words, (x) stands for the spatial dependency of the B1 field distribution.

In the case A), the first and second RF pulse were selected such that the signal S1 resulting after the second RF pulse is optimized in a desired manner. Only the signal S1 is measured and—if a sufficient number of signals S1 (for example in order to cover a desired positional space) have been measured—an optimized MR image can be calculated from them. Here the optimized MR image is thus calculated precisely from the signal S1 per pulse sequence $(\alpha 1,\phi 1)(x)$, $(\alpha 2,\phi 2)(x)$ which was acquired after the last radiated RF pulse $(\alpha 2,\phi 2)(x)$.

In the case B) the first and second RF pulse were optimized as in case A) only with regard to the signal S1; however, in spite of this a signal N1 is measured after the first RF pulse without the first RF pulse having to satisfy any conditions at all with regard to this signal N1. Although the signal N1 is "any" signal, without defined information content, such signals N1 can be used in order to obtain additional information about the examination subject and the prevailing measurement conditions. For example, signals N1 can be used as what are known as navigators and, for example, can be drawn upon for a movement correction of the acquired data from the signals S1. An additional example would be the use of signals N1 to calculate a B0 map, i.e. to determine the actual basic magnetic field B0 prevailing in the examination volume. In the last case two echoes could be acquired per signal N1, for example, in order to calculate the phase difference of these given unvarying amplitude of the echoes.

In case C) the first RF pulse has now already been selected under consideration of desired properties of the signal S2 but also together with the second RF pulse with regard to the signal S1 resulting after radiation of the second RF pulse. Two "full-fledged" signals S1 and S2 are thus obtained from which a respective first and second individual image can be calculated. However, as illustrated above the two individual images are dependent on one another. The individual images can now be calculated to form an optimized MR image, wherein an improved signal-to-noise ratio (SNR) can also hereby be achieved via the larger data set as a basis of the optimized MR image.

FIG. 4 shows an example of a calculation of two signal data sets (image data sets), obtained after a first RF pulse $(\alpha 1,\phi 1)(x)$ and a second RF pulse $(\alpha 2,\phi 2)(x)$, to form an optimized MR image. The B1 field distribution corresponding to the first and second RF pulse $(\alpha 1,\phi 1)(x)$ and $(\alpha 2,\phi 2)(x)$ is shown in the two upper images, depending on the location x. If these two RF pulses $(\alpha 1,\phi 1)(x)$ and $(\alpha 2,\phi 2)(x)$ are always applied again one after another and at sufficiently short time intervals, steady state signals form after every RF pulse, which steady state signals correspond to the magnetizations M1 and M2 shown in the lower images.

In the present case the first RF pulse and the second RF pulse were selected such that the magnetization M1 achieved after the first RF pulse and the magnetization M2 achieved after the second RF pulse and dependent on the magnetization M1 yield, after addition of the magnetizations, an optimized, optimally homogeneous magnetization M_o. Accordingly, via addition of image data acquired after the first RF pulse with image data acquired after the second RF pulse an optimized image data set is obtained that corresponds to an image data set acquired given an optimized magnetization M_o. Two signals respectively resulting after one of the radiated RF pulses were thus hereby acquired, and from this individual images were initially calculated that are subject to a calculation to form an optimized image.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating an optimized magnetic resonance image of an examination subject, comprising:
    placing an examination subject in a magnetic resonance data acquisition unit comprising a plurality of radio frequency (RF) transmission coils;
    operating said plurality of RF transmission coils in parallel to radiate at least two RF excitation pulses into the examination subject in the data acquisition unit, that each excite nuclear spins in the subject to cause emission of at least one magnetic resonance signal from the nuclear spins in the subject that have been excited by said at least two RF excitation pulses, with at least a second of said RF excitation pulses being radiated before an effect on said nuclear spins of a preceding RF excitation pulse in said series of at least two RF excitation pulses has subsided, so that said at least one magnetic resonance signal comprises signal contributions from nuclear spins excited by said preceding RF excitation pulse and nuclear spins excited by said at least a second of said RF excitation pulses;
    selecting at least said preceding RF excitation pulse and said at least a second of said RF excitation pulses to cause said signal contributions to give said magnetic resonance signal a selected optimization as an optimized magnetic resonance signal;
    spatially encoding said at least one optimized signal with a spatial coding;
    detecting the at least one optimized and spatially coded magnetic resonance signal with a reception antenna of said data acquisition unit;
    repeating radiation of said sequence and modifying said spatial coding with each repetition until all signals have been generated and acquired in a predetermined region of the examination subject; and
    in a processor, calculating a magnetic resonance image for each pulse sequence from at least one of the acquired signals, said magnetic resonance image having an image content that is a result of said selected optimization given to said optimized magnetic resonance signal.

2. A method as claimed in claim 1 comprising selecting the radiated RF excitation pulses to give said optimized magnetic resonance image a predetermined image contrast.

3. A method as claimed in claim 1 comprising calculating said optimized magnetic resonance image for each pulse sequence from only said signal acquired after a last radiated RF excitation pulse in said sequence.

4. A method as claimed in claim 1 comprising in each pulse sequence, acquiring at least two signals that occur after each radiated RF excitation pulse and, from said at least two signals arising after each radiated RF excitation pulse, reconstructing individual images and forming said optimized MR image from the reconstructed individual images.

5. A method as claimed in claim 1 comprising obtaining additional information about the examination subject in each pulse sequence from at least one of the acquired signals.

6. A method as claimed in claim 1 comprising acquiring the optimized magnetic resonance signals with parallel reception coils, as said reception antenna, in said data acquisition unit.

7. A magnetic resonance system comprising:
    a magnetic resonance data acquisition unit comprising a plurality of radio frequency (RF) transmission coils, and a reception antenna;
    a control unit configured to operate said data acquisition unit by providing signals to said plurality of RF transmission coils in parallel to cause said RF transmission coils to radiate at least two RF excitation pulses into an examination subject located in the data acquisition unit, causing that each excite nuclear spins in the subject so as to cause emission of at least one optimized magnetic resonance signal from nuclear spins in the subject that have been excited by said at least two RF excitation pulses, with at least a second of said RF excitation pulses being radiated before an effect on said nuclear spins of a preceding RF excitation pulse in said series of at least two RF excitation pulses has subsided, so that said at least one magnetic resonance signal comprises signal contributions from nuclear spins excited by said preceding RF excitation pulse and nuclear spins excited by said second of said RF excitation pulses;

select at least said preceding RF excitation pulse and said at least a second of said RF excitation pulses to cause said signal contributions to give said magnetic resonance signal a selected optimization as an optimized magnetic resonance signal;

a gradient coil system operated by said control unit to spatially encode said at least one optimized signal with a spatial coding;

said control unit being configured to operate said data acquisition unit to detecting the at least one optimized and spatially coded magnetic resonance signal with a reception antenna of said data acquisition unit;

said control unit being configured to operate said data acquisition unit to repeat radiation of said sequence and modifying said spatial coding with each repetition until all signals have been generated and acquired in a predetermined region of the examination subject; and a processor configured to calculate an optimized magnetic resonance image for each pulse sequence from at least one of the acquired signals, said magnetic resonance image having an image content that is a result of said selected optimization given to said optimized magnetic resonance signal.

8. A non-transitory, computer-readable storage medium encoded with programming instructions, said storage medium being loaded into a computerized control and evaluation system of a magnetic resonance system having a data acquisition unit having a plurality of radio frequency (RF) transmission coils, said programming instructions causing said computerized control and evaluation system to:

operate said plurality of RF transmission coils in parallel to radiate at least two RF excitation pulses into an examination subject located in the data acquisition unit, to cause emission of at least one optimized magnetic resonance signal from nuclear spins in the subject that have been excited by said at least two RF excitation pulses, with at least a second of said RF excitation pulses being radiated before an effect on said nuclear spins of a preceding RF excitation pulse in said series of at least two RF excitation pulses has subsided, so that said at least one magnetic resonance signal comprises signal contributions from nuclear spins excited by said preceding RF excitation pulse and nuclear spins excited by said second of said RF excitation pulses;

select at least said preceding RF excitation pulse and said at least a second of said RF excitation pulses to cause said signal contributions to give said magnetic resonance signal a selected optimization as an optimized magnetic resonance signal;

spatially encode said at least one optimized signal with a spatial coding;

detect the at least one optimized and spatially coded magnetic resonance signal with a reception antenna of said data acquisition unit;

repeat radiation of said sequence and modifying said spatial coding with each repetition until all signals have been generated and acquired in a predetermined region of the examination subject; and calculate an optimized magnetic resonance image for each pulse sequence from at least one of the acquired signals, said magnetic resonance image having an image content that is a result of said selected optimization given to said optimized magnetic resonance signal.

\* \* \* \* \*